United States Patent
Almo et al.

(10) Patent No.: US 12,258,304 B2
(45) Date of Patent: Mar. 25, 2025

(54) COMPOUNDS AND METHODS FOR TREATMENT OF BACTERIAL INFECTIONS

(71) Applicants: Albert Einstein College of Medicine, Bronx, NY (US); Victoria Link Limited, Wellington (NZ)

(72) Inventors: Steven C. Almo, Pelham, NY (US); Tyler Grove, Bronx, NY (US); Lawrence D. Harris, Lower Hutt (NZ); Gary B. Evans, Lower Hutt (NZ)

(73) Assignees: Albert Einstein College of Medicine, Bronx, NY (US); Victoria Link Limited, Wellington (NZ)

( * ) Notice: Subject to any disclaimer, the term of this patent is extended or adjusted under 35 U.S.C. 154(b) by 745 days.

(21) Appl. No.: 17/612,647

(22) PCT Filed: May 20, 2020

(86) PCT No.: PCT/US2020/033756
§ 371 (c)(1),
(2) Date: Nov. 19, 2021

(87) PCT Pub. No.: WO2020/236907
PCT Pub. Date: Nov. 26, 2020

(65) Prior Publication Data
US 2022/0234995 A1 Jul. 28, 2022

Related U.S. Application Data

(60) Provisional application No. 62/850,245, filed on May 20, 2019.

(51) Int. Cl.
*C07C 229/38* (2006.01)
*A61P 31/04* (2006.01)
*C07C 63/14* (2006.01)
*C07C 323/62* (2006.01)
*C07D 213/79* (2006.01)

(52) U.S. Cl.
CPC .......... *C07C 229/38* (2013.01); *A61P 31/04* (2018.01); *C07C 63/14* (2013.01); *C07C 323/62* (2013.01); *C07D 213/79* (2013.01)

(58) Field of Classification Search
CPC ......... C07C 229/38; C07C 63/14; A61P 31/04
See application file for complete search history.

(56) References Cited

U.S. PATENT DOCUMENTS 8,114,648 B2   2/2012   Schultz et al.

FOREIGN PATENT DOCUMENTS

GB   2404855 A   2/2005

OTHER PUBLICATIONS

Bulloch et al., 'Identification of 4-Amino-4-deoxychorismate Synthase as the Molecular Target for the Antimicrobial Action of (6S)-6-Fluoroshikimate', J. Am. Chem. Soc. 2004, vol. 126, pp. 9912-9913. p. 9912, Scheme 1.
Gonzalez-Bello, 'Recently Developed Synthetic Compounds with Anti-infective Activity', Current Opinion in Pharmacology, 2019, vol. 48, pp. 17-23 [Available online Apr. 18, 2019].
Joshi et al., 'Antibacterial Strategy Against H.Pylori: Inhibition of the Radical SAM Enzyme MqnE in Menaquinone Biosynthesis', ACS Medicinal Chemistry letters, Feb. 15, 2019 (Feb. 15, 2019) vol. 10, pp. 363-366.
Mahanta et al., 'Menaquinone Biosynthesis: Formation of Aminofutalosine Requires a Unique Radical SAM Enzyme', J. Am. Chem. Soc. 2013, vol. 135, pp. 15318-15321.
International Search Report and Written Opinion mailed Aug. 14, 2020 for International Application No. PCT/US20/33756, 7 pages.

*Primary Examiner* — Kamal A Saeed
(74) *Attorney, Agent, or Firm* — Fox Rothschild LLP

(57) ABSTRACT

This document discloses a novel class of compounds for inhibiting bacterial growth and treating bacterial infection. The compounds target a key step of the futalosine pathway and therefore are effective for the selective inhibition of certain bacterial species and genera with reduced side effect in comparison with conventional antibiotics.

20 Claims, 5 Drawing Sheets

COMPOUNDS AND METHODS FOR TREATMENT OF BACTERIAL INFECTIONS

CROSS-REFERENCE TO RELATED APPLICATIONS

This application is a national stage application filed under 35 U.S.C. § 371 of PCT/US20/33756 which claims the benefit of U.S. Provisional Patent Application Ser. No. 62/850,245, filed on May 20, 2019. The entire contents of these applications are incorporated herein by reference in their entireties.

STATEMENT REGARDING FEDERALLY SPONSORED RESEARCH OR DEVELOPMENT

This invention was made with government support under Grant Nos. P01 GM118303-01, R21 AI133329, U54 GM093342, and U54 GM094662 awarded by the National Institutes of Health and National Institute of General Medical Sciences. The government has certain rights in the invention.

TECHNICAL FIELD

Disclosed herein is a novel class of compounds that selectively target and kill certain families of bacteria. The compounds inhibit a key step in the futalosine pathway for bacteria proliferation.

BACKGROUND OF THE INVENTION

While the prevalence of multi-drug resistant pathogens continues to rise, the rate at which new clinical antimicrobials are introduced has declined significantly. In addition, the treatment of persistent infections has been complicated by pathogen phenotypes. Bacteria that grow very slowly are often associated with prolonged infections, and they are particularly tolerant to many of the clinically important classes of antibiotics that inhibit rapidly growing cells.

Considerable antibiotic resistance has emerged in *Campylobacter* species, including significant resistance to first line macrolides (e.g., azithromycin), fluoroquinolones (e.g., ciprofloxin), aminoglycosides, and betalactam antibiotics. For instance, *Campylobacter jejuni* (C), a gram-negative bacterium, is believed to be the primary cause of gastrointestinal disorders and is linked to the development of Guillain-Barre Syndrome, a chronic autoimmune disorder. The closely related *Helicobacter pylori* (Hp) is present in about 50% of the population in developed countries. Individuals with Hp infections have an eight-fold greater risk of developing stomach cancer than those who are uninfected, which ultimately leads to almost 600,000 cases of gastric cancer every year. Treatment of Hp-induced gastro-intestinal ulcers with a three-drug cocktail, which includes clarithromycin, metronidazole (Mtz), and a proton pump inhibitor (e.g., omeprazole), is showing reduced effectiveness. Thus, the incidence of Hp resistant to clarithromycin and Mtz has steadily risen to greater than 20%, underscoring the need for new therapeutic targets and new antibiotics. Of equal importance is the need to develop more targeted approaches that minimally perturb the overall health of the resident gut microbiome, so as to minimize opportunistic pathogens like *Clostridium difficile*, which can further complicate treatment by infecting patients and causing pseudomembranous colitis. These subsequent infections largely arise from the use of broad-spectrum antibiotics like clarithromycin, Mtz, and vancomycin, which decimate the natural gut microbiota milieu and allow opportunistic pathogens to proliferate.

Thus, improved and alternative antibacterial agents are urgently needed.

BRIEF SUMMARY OF THE INVENTION

In accordance with the present disclosure, for the first time radical S-adenosyl-L-methionine (RS) enzymes have been identified as a viable drug target. Currently there are 225,000 RS enzymes known, most of which are found in bacteria. By targeting critical catalytic pathways of RS enzymes, the present invention provides a unique approach to selective bacterial inhibition.

An aspect of this invention provides a compound or a pharmaceutically acceptable salt thereof, wherein the compound is represented by Formula I,

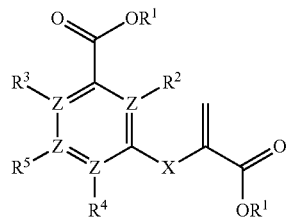

wherein:
$R^1$ in each instance independently is hydrogen or $C_{1-10}$alkyl, wherein the $C_{1-10}$alkyl is optionally substituted with a halogen, oxo (=O), OH, $OC_{1-4}$alkyl, $SC_{1-4}$alkyl, or aryl$C_{1-6}$alkyl;
$R^2$, $R^3$, $R^4$, and $R^5$ are each independently selected from the group consisting of hydrogen, fluorine, chlorine, bromine, $C_{1-4}$alkyl, CN, $C_{1-6}$alkylCONH, $C_{1-6}$alkylNHCO, $C_{1-6}$alkylSO$_2$NH, $C_{1-6}$alkylNHSO$_2$, and $C_{1-6}$alkylSO$_2$;
X is O, S, NH or CH$_2$; and
Z in each instance independently is C or N;
provided that when a Z is N, the substituent attached thereto ($R^2$, $R^3$, $R^4$, or $R^5$) is void, and when each Z is C, at least one of $R^2$, $R^3$, $R^4$, and $R^5$ is chlorine or fluorine.

Another aspect of the invention provides a pharmaceutical composition or a kit comprising a therapeutically effective amount of a compound as disclosed herein or a pharmaceutically acceptable salt thereof. In some embodiments, the composition or the kit further includes an additional agent.

Another aspect of this document provides a method of treating at least one of influenza A and influenza B using a compound described herein or a pharmaceutically acceptable salt thereof.

Another aspect of the invention provides a method of inhibiting the proliferation of bacteria in a subject in need thereof. The method includes administering to the subject a therapeutically effective amount of a compound or a pharmaceutically acceptable salt thereof of described herein. The proliferation may involve the futalosine pathway.

Another aspect of the invention provides a method of inhibiting the proliferation of bacteria in a medium. The method includes contacting the medium with an effective amount of a compound or the pharmaceutically acceptable salt thereof described herein. The proliferation may involve the futalosine pathway.

Another aspect of the invention provides a method of inhibiting MqnE in a bacterial cell by contacting the cell with an effective amount of the compound or the pharmaceutically acceptable salt thereof described herein.

BRIEF DESCRIPTION OF THE DRAWINGS

FIG. 1 (a) shows the proposed mechanism and FIG. 1(b) shows fluorinated analogues of DHC. DHC, dehydrochorismate.

FIG. 2(a) shows activity of PhMqnE in the presence of 1 mM SAM, 2 mM DHC alone, or mixed with 2 mM inhibitor. FIG. 2(b) shows activity of PhMqnE in the presence of 1 mM SAM, 2 mM DHC or 2 mM fluorinated-DHC analogs. AF, aminofutalosine; I1, intermediate that builds up during turnover with 2-FDHC, Cpd X, compound X. No product was detectable in reactions with only 2,4-FDHC. FIG. 2(c) shows inhibition of AF production by increasing concentration of 2F-DHC. Assays contained 0.5 μM of PhMqnE, 1 mM SAM, 1 mM DHC, and 2-FDHC varied from 5 μM to 2 mM.

FIG. 3(a) shows inhibition of Hp growth by 2F-DHC. The inhibition of Hp growth in the presence of increasing concentrations of 2F-DHC was determined by measuring the $OD_{600}$ of liquid cultures incubated at 37° C. for 72 hours. FIG. 3(b) shows that Hp is fully inhibited by 1 mM 2F-DHC, but adding 1 mM of AF (MqnE) can restore growth in the presence of 1 mM 2F-DHC. Inhibition was determined by measuring the $OD_{600}$ of liquid cultures incubated at 37° C. for 48 hours.

FIG. 4(a) shows the growth of an overnight culture of *E. coli*, which was diluted 1:25 into 100 μL of minimal media with either 1 μL of DMSO (no DHC control) or 1 μL of 100 mM 2F-DHC in DMSO in a 96-well plate. FIG. 4(b) shows a 24 and 48 hr culture of HEK293T cells grown in FreeStyle Expression Medium containing either 1% DMSO (no DHC control) or 1 mM 2F-DHC in DMSO in a 24-well plate.

DETAILED DESCRIPTION OF THE INVENTION

Figure 1A:
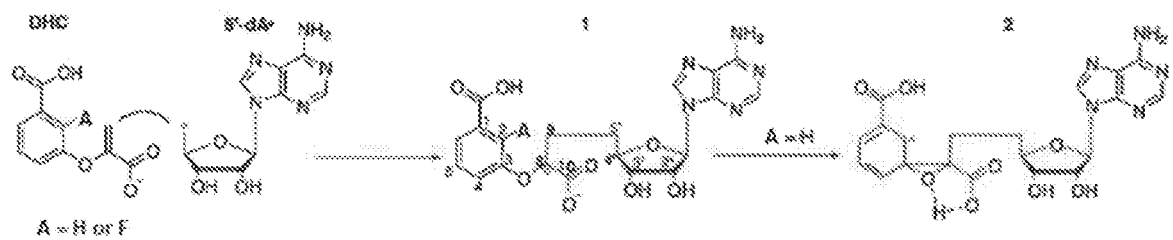
FIGS. 1(a) and 1(b) illustrate the proposed mechanism for the production of aminofutalosine (AF) catalyzed by MqnE.

The compounds disclosed herein target pathways specific to distinct species of pathogenic bacteria to inhibit their proliferation. Through inhibition of RS enzymes catalyzed production of Menaquinone (MK), certain families of bacteria can be effectively eliminated. MK is an obligate lipid-soluble cofactor essential for function of the respiratory chain in bacteria. MK is typically derived from chorismate by the action of the men operon found in a wide range of bacterial species. However, it was recently discovered that a subset of bacterial species, including Cj and Hp, lack the enzymes necessary to produce MK through this conventional pathway, and instead utilize an alternative pathway termed the futalosine pathway. Two key steps in this alternative pathway are catalyzed by radical S-adenosyl-L-methionine enzymes: MqnE produces aminofutalosine (AF) by catalyzing the coupling of SAM and 3-[(1-carboxyvinyl)oxy]-benzoic acid (dehydrochorismate or DHC), while MqnC produces cyclic dehypoxanthine futalosine from dehypoxanthine futalosine. MqnE, in particular, has been studied extensively and is believed to play a key role in bacteria proliferation. By intervening in the futalosine pathway and suppressing the production of MK, inhibition and elimination of bacteria can be achieved.

While the following text may reference or exemplify specific embodiments of a compound or a method of treating a disease or condition, it is not intended to limit the scope of the compound or method to such particular reference or examples. Various modifications may be made by those skilled in the art, in view of practical and economic considerations, such as the substitutions of the compound and the amount or administration of the compound for treating or preventing bacterial infection.

The articles "a" and "an" as used herein refer to "one or more" or "at least one," unless otherwise indicated. That is, reference to any element or component of an embodiment by the indefinite article "a" or "an" does not exclude the possibility that more than one element or component is present.

The term "pharmaceutical composition" refers to a mixture of a compound disclosed herein with other chemical components, such as diluents or additional carriers. The pharmaceutical composition facilitates administration of the compound to an organism. Multiple techniques of administering a pharmaceutical composition exist in the art including, but not limited to, oral, injection, aerosol, parenteral, and topical administration. In some embodiments, pharmaceutically acceptable salts of the compounds disclosed herein are provided.

The term "carrier" refers to a chemical compound that facilitates the incorporation of a compound into cells or tissues.

The term "diluent" refers to chemical compounds diluted in water that will dissolve the composition of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound. As used herein, an "excipient" refers to an inert substance that is added to a composition to provide, without limitation, bulk, consistency, stability, binding ability, lubrication, disintegrating ability, etc., to the composition. A "diluent" is a type of excipient.

The term "physiologically acceptable" or "pharmaceutically acceptable" refers to a carrier or diluent that does not abrogate the biological activity and properties of the compound.

The term "subject" refers to a human or an animal.

The term "effective amount" or "therapeutically effective amount" refers to an amount of a compound effective to inhibit bacterial growth, or prevent, alleviate or ameliorate symptoms of disease or prolong the survival of the subject being treated. Determination of a therapeutically effective amount is well within the capability of those skilled in the art, especially in light of the detailed disclosure provided herein.

The term "alkyl" refers to linear or branched carbon chain particularly having up to about 18 carbon atoms, more particularly as a lower alkyl, from 1 to 10 carbon atoms and still more particularly, from 1 to 6 carbon atoms. The hydrocarbon chain may be either straight-chained or branched. The term "$C_{1-10}$ alkyl" refers to alkyl groups having 1, 2, 3, 4, 5, 6, 7, 8, 9 or 10 carbon atoms. Non-limiting examples include groups such as methyl, ethyl, n-propyl, isopropyl, n-butyl, iso-butyl, tert-butyl, and the like. An alkyl group can be further substituted with groups such as halogen, oxo (=O), OH, $OC_{1-6}$alkyl, $SC_{1-6}$alkyl, and alkylaryl$C_{1-6}$alkyl. Non-limiting examples of halogen substituted alkyl include $CH_2CH_2Cl$ and $CHF_2$. When an alkyl is substituted with an oxo, the resulting substituent may contain a ketone or an aldehyde. When an alkyl is substituted with $OC_{1-4}$alkyl or $SC_{1-6}$alkyl, the resulting substituent contains an ether or thioether moiety. Examples of additional aryl$C_{1-6}$alkyl includes benzylic group and $CH_2CH_2Ph$. The position and method for introducing additional substitutions to the alkyl group can be determined by one of ordinary skill in the art in view of common knowledge in synthetic organic chemistry.

The term "aryl" refers to optionally-substituted monocyclic and fused bicyclic hydrocarbyl moiety. Any monocyclic or fused ring bicyclic system which has the characteristics of aromaticity in terms of electron distribution throughout the ring system is included in this definition.

The term "treating" or "treatment" of any disease or condition refers, in some embodiments, to ameliorating the disease or disorder (i.e., arresting or reducing the development of the disease or at least one of the clinical symptoms thereof). In some embodiments "treating" or "treatment" refers to ameliorating at least one physical parameter, which may not be discernible by the subject. In some embodiments, "treating" or "treatment" refers to modulating the disease or disorder, either physically, (e.g., by stabilization of a discernible symptom), physiologically, (e.g., by stabilization of a physical parameter), or both. In some embodiments, "treating" or "treatment" refers to delaying the onset of the disease or disorder, or even preventing the same. "Prophylactic treatment" is to be construed as any mode of treatment that is used to prevent progression of the disease or is used for precautionary purpose for persons at risk of developing the condition.

An aspect of the invention provides a compound or a pharmaceutically acceptable salt thereof for the inhibition of bacterial proliferation, wherein the compound is represented by Formula I:

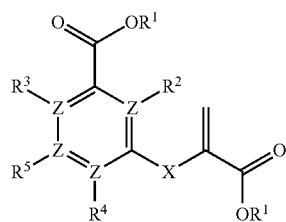

Formula I wherein:
$R^1$ in each instance independently is hydrogen or $C_{1-10}$alkyl, wherein the $C_{1-10}$alkyl is optionally substituted with a halogen, oxo (=O), OH, $OC_{1-4}$alkyl, $SC_{1-4}$alkyl, or aryl$C_{1-6}$alkyl;
$R^2$, $R^3$, $R^4$, and $R^5$ are each independently selected from the group consisting of hydrogen, fluorine, chlorine, bromine, $C_{1-4}$alkyl, CN, $C_{1-6}$alkylCONH, $C_{1-6}$alkylNHCO, $C_{1-6}$alkylSO$_2$NH, $C_{1-6}$alkylNHSO$_2$, and $C_{1-6}$alkylSO$_2$;
X is O, S, NH or $CH_2$; and
Z in each instance independently is C or N, provided that when a Z is N, the substituent attached thereto ($R^2$, $R^3$, $R^4$, or $R^5$) is void, and when each Z is C, at least one of $R^2$, $R^3$, $R^4$, and $R^5$ is chlorine or fluorine.

In some embodiments of Formula I, the compound is represented by Formula I-a:

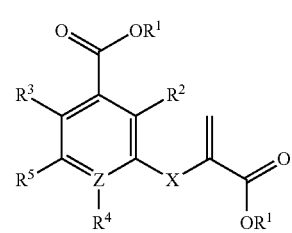

Formula I-a wherein the substituents are as define above. In some embodiments of I-a, $R^1$ is H.

In some embodiments of Formula I, the compound is represented by Formula I-b:

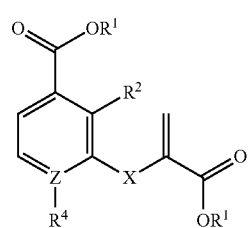

Formula I-b wherein Z—$R^4$ is CH or N, and the other substituents are as described above. In some embodiments of I-b, $R^1$ is H.

In some embodiments of Formula I, the compound is represented by Formula I-c. The substituents are as described above.

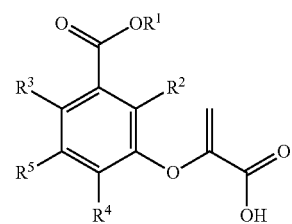

Formula I-c

In some embodiments of Formula I-c, $R^1$ is H.

In some embodiments of Formula I, I-a, I-b or I-c, $R^1$ is hydrogen or $C_{1-6}$alkyl; $R^2$, $R^3$, $R^4$, and $R^5$ are each independently selected from the group consisting of hydrogen, fluorine, chlorine, and $C_{1-6}$alkyl; and provided that at least one of $R^2$, $R^3$, $R^4$, and $R^5$ is chlorine or fluorine.

In some embodiments of Formula I, I-a, I-b or I-c, $R^1$ is hydrogen. In some embodiments, $R^1$ is $C_{1-6}$alkyl. In some embodiments, at least one of $R^2$, $R^3$, $R^4$, and $R^5$ is fluorine, and the others are independently hydrogen, fluorine, chlorine, or $C_{1-6}$alkyl. In some embodiments, $R^2$, $R^3$, $R^4$, and $R^5$ are each independently hydrogen or fluorine.

In some embodiments of Formula I, I-a, I-b or I-c, $R^1$ is hydrogen, and at least one of $R^2$, $R^3$, $R^4$, and $R^5$ is fluorine. In some embodiments, $R^1$ is hydrogen, at least one of $R^2$, $R^3$, $R^4$, and $R^5$ is fluorine, and the others of $R^2$, $R^3$, $R^4$, and $R^5$ are hydrogen. In some embodiments, $R^1$ and $R^3$ are each hydrogen or fluorine, and $R^2$, $R^4$, and $R^5$ are each a hydrogen or fluorine.

Non-limiting examples of the compounds of Formula I include the following:

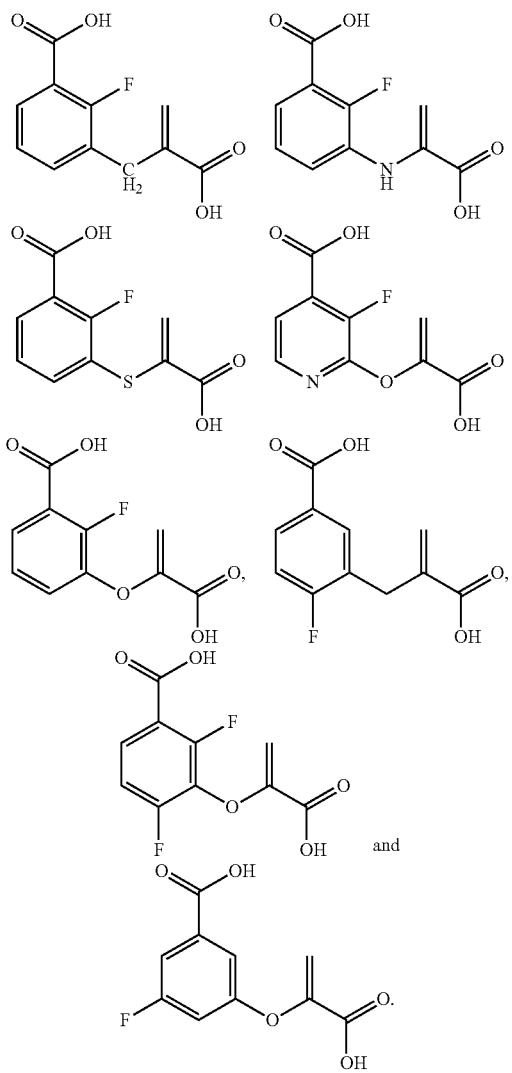

In one preferred embodiment, the compound is

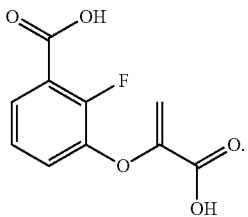 [SMILES: C=C(Oc1cccc(C(=O)O)c1F)C(=O)O]

Another aspect of the present disclosure provides a pharmaceutical composition containing a therapeutically effective amount of an above-described compound or a salt thereof and a pharmaceutically acceptable carrier. In some embodiments, the pharmaceutical composition can further include one or more additional antibacterial agents. Non-limiting examples of the additional agent include metronidazole, amoxicillin, clarithromycin, Rabeprazole (a substituted benzimidazole proton pump inhibitor) and other proton pump inhibitors.

The pharmaceutical composition may also contain one or more physiologically acceptable surface active agents, additional carriers, diluents, excipients, smoothing agents, suspension agents, film forming substances, and coating assistants, or a combination thereof. Acceptable additional carriers or diluents for therapeutic use are well known in the pharmaceutical art, and are described, for example, in Remington's Pharmaceutical Sciences, 18th Ed., Mack Publishing Co., Easton, PA (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, microcrystalline cellulose, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The pharmaceutical compositions may be manufactured in a manner that is itself known, e.g., by means of conventional mixing, dissolving, granulating, dragee-making, levigating, emulsifying, encapsulating, entrapping or tabletting processes.

The compound of Formula I or the pharmaceutically acceptable salt thereof or the pharmaceutical composition thereof described herein may, if desired, be presented in a kit, a pack or a dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound formulated in a compatible pharmaceutical carrier may also be prepared, placed in an appropriate container, and labeled for treatment of an indicated condition.

The kit, pack, or dispensing device may contain one or more additional agents such as an antibiotic agent or a proton pump inhibitor. For example, the antibiotic agent or antibacterial agent can be one of penicillins, bismuth compounds, tetracyclines, nitroimidazoles, quinolones, lincosamides, macrolides and cephalosporins, any pharmaceutically acceptable salt thereof, solvates thereof, and any combinations of the foregoing.

Examples of the penicillins include, but are not limited to, penicillin G, penicillin V, pheneticillin, propicillin, methicillin, oxacillin, cloxacillin, dicloxacillin, flucloxacillin, nafcillin, ampicillin, amoxycillin, bacampicillin, hetacillin, metampicillin, pivampicillin, talampicillin, carbenicillin, carfecillin, carindacillin, sulbenicillin, ticarcillin, azlocillin, mezlocillin, piperacillin, apalcillin, temocillin, mecillinam, and pivmecillinam, any pharmaceutically acceptable salt thereof, solvates thereof, and any combinations of the foregoing.

Additional agents that can be used in combination with the compound of Formula I include for example metronidazole, amoxicillin, clarithromycin, Rabeprazole (a substituted benzimidazole proton pump inhibitor) and other proton pump inhibitors.

Examples of macrolides include, but are not limited to, erythromycin, spiramycin, oleandomycin, triacetyloleandomycin, clarithromycin, roxithromycin, josamycin, kitsamycin, midecamycin, miocamycin, rokitamycin, dirithromycin, rosarimycin, flurithromycin, and azithromycin, any pharmaceutically acceptable salt thereof, solvates thereof, and any combinations of the foregoing.

Examples of cephalosporins include, but are not limited to, cephalexin, pivcephalexin, cephalothin, cephazolin, cefroxadine, cefadroxil, cefatrizine, cefaclor, cefprozil, cephradine, and second as well as third generation cephalosporins such as cephamandole, cefuroxime, cefuroxime axetil, cefonicid, ceforanide, cefotiam, cefotaxime, cefinenoxime, cefodizime, ceftizoxime, cefiximine, cefdinir, cefetamet pivoxil, cefpodoxime proxetil, ceftibuten, ceftazidime, ceftoperazone, cefpiramide, cefsoludin, cefepime, cefpirome, and ceftriaxone, and related compounds such as oxycephalosporins including latamoxef, and cephamycins such as cefoxitin, cefmetazole, cefotetan, cefbuperazone, and cefminox, any pharmaceutically acceptable salt thereof, solvates thereof, and any combinations of the foregoing.

Another aspect of the present disclosure provides a method of treating bacterial infection or inhibiting the proliferation of a specific bacterial species, or subset of bacterial species, in a subject in need thereof. The proliferation of the bacterial species should involve the futalosine pathway to effect species selectivity. The method includes administering to the subject a therapeutically effective amount of a compound or a pharmaceutically acceptable salt thereof described herein or the pharmaceutical composition thereof described herein.

Without being bound by any particular theory, it is postulated that the compounds disclosed herein form a stabilized intermediate along the futalosine pathway, thereby acting as mechanism-based inhibitor and trapping the requisite enzyme in an intermediate state. A proposed mechanism is illustrated in FIG. 1. Under the catalysis of MqnE, the 5'-deoxyadenosyl-radical (5'-dA.) derived from reductive cleavage of SAM adds directly to the vinyl position of DHC, which forms a captodative radical intermediate (1 in FIG. 1). When A is hydrogen, spiroepoxide formation with the neighboring benzene ring generates a resonance-stabilized radical species. Subsequent rearrangement, followed by decarboxylation, results in a radical anion species that can undergo a one-electron reduction by the [4Fe-4S] cluster of MqnE to produce AF. However, when A is F, the stabilized captodative radical intermediate would prevent or limit further conversion to intermediate 2, essentially trapping the enzyme in an intermediate state.

By targeting the futalosine pathway specific to distinct species of pathogenic bacteria, the antibiotics of the present invention have significant advantages over conventional antibiotic regimens. For instance, the more targeted approach described herein minimally perturbs the overall health of the resident gut microbiome, so as to minimize opportunistic pathogens like *Clostridium difficile*, which can further complicate treatment by infecting patients and causing pseudomembranous colitis. These subsequent infections largely arise from the use of broad-spectrum antibiotics like clarithromycin, Mtz, and vancomycin, which decimate the natural gut microbiota milieu and allow opportunistic pathogens to proliferate. Therefore, the target specific method of the present invention offers a unique and effective approach to limit the opportunistic infections.

In some embodiments, the method targets the futalosine pathway to inhibit the production of aminofutalosine (AF). In some embodiments, the production of the aminofutalosine is catalyzed by radical SAM enzyme. In some embodiments, the radical SAM enzyme is MqnE, which is inhibited by the compounds described herein.

The selective inhibition approach impacts minimally to some bacteria species such as *Clostridium difficile, Escherichia coli* and other host resident bacterial species lacking the futalosine pathway. In some embodiments, the method of the present invention is active and selective for a bacterial genus including for example *Helicobacter* and *Campylobacter*, as well as members of the genera *Streptococcus. Clostridium. Mycoplasma, Lactobacillus, Staphylococcus. Bifidobacterium, Rickettsia*, and *Brucella*. In some embodiments, the method is effective against the *Helicobacter* genus. In some embodiments, the method is selective for *Helicobacter pylori*.

In some embodiments, the subject receiving the administration of the compound, a pharmaceutically acceptable salt thereof or a pharmaceutical composition thereof is a human. In some embodiments, the subject is an animal.

In some embodiments, the compound is selected from the group consisting of

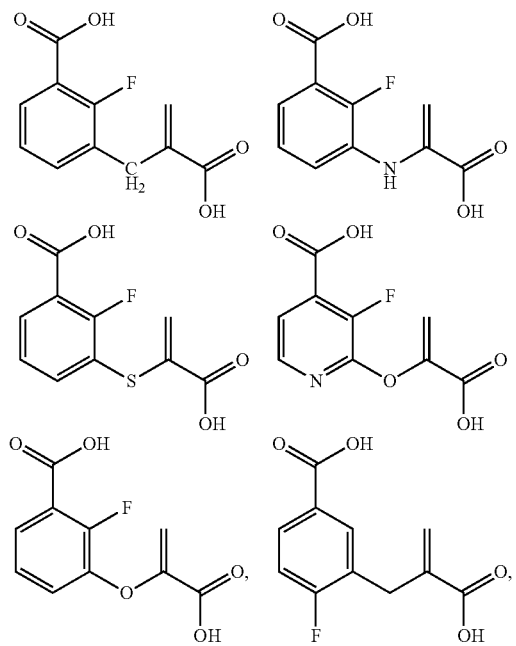

-continued

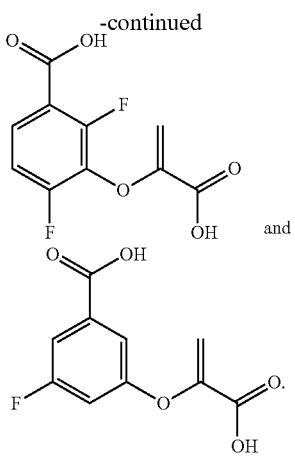

In some embodiments, the compound is

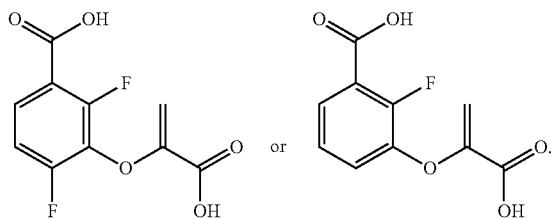 [SMILES: C=C(Oc1c(F)ccc(C(=O)O)c1F)C(=O)O ; C=C(Oc1cccc(C(=O)O)c1F)C(=O)O]

In some embodiments the compound is

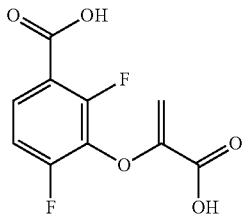 [SMILES: C=C(Oc1c(F)ccc(C(=O)O)c1F)C(=O)O]

and the bacteria is *Helicobacter pylori*.

In some embodiments, the method further includes administering to the subject one or more additional agents including for example an antibacterial agent and a proton pump inhibitor, which may be selected from a number of suitable agents, sources, or brands known in the art as described above.

The mechanism of action of antibiotics, in the case of *H. pylori*, is thought to be both local at the site of infection in the gastric tissue, and systemic, including via reuptake of the antimicrobial agents to gastric tissue from the blood. As such, gastric release of the antibiotics is essential for effective treatment. However, antibiotics are generally more stable in mildly acidic to basic condition, and can sensitive to degradation of gastric acid. The proton pump inhibitors (PPIs) are drugs capable of reducing gastric acid production by, for example, inhibiting the hydrogen/potassium adenosine triphosphatase enzyme system of the gastric parietal cell. Therefore, addition of PPI (e.g., omeprazole) which suppresses the production of stomach acid can increase intra-gastric pH, and thereby decrease the degradation of the antibiotics to further help the anti-*H pylori* effects. PPIs are however acid-unstable and can be sensitive to degradation by gastric acid. The PPI in the compositions of the present invention is formulated for intestinal release to avoid its rapid degradation in the acidic gastric environment.

A related aspect of the patent document provides a method of the catalytic activities of MqnE in a bacterial cell. The method includes contacting the cell with an effective amount of the compound or the pharmaceutically acceptable salt thereof described herein. In some embodiments, the bacteria cell belongs to a genus selected from *Helicobacter, Campylobacter, Streptococcus. Clostridium. Mycoplasma, Lactobacillus, Staphylococcus. Bifidobacterium, Rickettsia*, and *Brucella*. In some embodiments, the bacteria is *Helicobacter pylori*.

The compound of Formula I or its pharmaceutically acceptable salt can be administered simultaneously or sequentially with the additional agents. When the agents are administered sequentially, the desirable interval between the administrations of different agents can be determined by one of ordinary skill in the art without undue experiments.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compound can also be administered in sustained or controlled release dosage forms, including depot injections, osmotic pumps, pills, transdermal (including electrotransport) patches, and the like, for prolonged and/or timed, pulsed administration at a predetermined rate.

For oral administration, the composition can be formulated readily by combining the compositions of interest with pharmaceutically acceptable carriers well known in the art as described above. Such carriers, which may be used in addition to the cationic polymeric carrier, enable the compositions to be formulated as tablets, pills, dragees, capsules, liquids, gels, syrups, slurries, suspensions and the like, for oral ingestion by a patient to be treated.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks' solution, Ringer's solution, or physiological saline buffer. If desired, absorption enhancing preparations may be utilized.

For buccal administration, the compositions may take the form of tablets or lozenges formulated in a conventional manner. Administration to the buccal mucosa and sublingually are contemplated.

For administration by inhalation, the composition can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compositions may also be formulated in rectal compositions such as suppositories or retention enemas, e.g., containing conventional suppository bases such as cocoa butter or other glycerides.

The therapeutically effective amount of the compound of Formula I or its pharmaceutically acceptable salt required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved adverse side effects disappear. The dosage may range broadly, depending upon the desired effects and the therapeutic indication. Typically, dosages may be about 10 microgram/kg to about 100 mg/kg body weight, preferably about 100 microgram/kg to about 10 mg/kg body weight. Alternatively dosages may be based and calculated upon the surface area of the patient, as understood by those of skill in the art.

The exact formulation, route of administration and dosage for the pharmaceutical compositions can be chosen by the individual physician in view of the subject's condition. (See e.g., Fingl et al. 1975, in "The Pharmacological Basis of Therapeutics", which is hereby incorporated herein by reference in its entirety, with particular reference to Ch. 1, p. 1). In some embodiments, the dose range of the composition administered to the subject can be from about 0.5 to about 1000 mg/kg of the patient's body weight. The dosage may be a single one or a series of two or more given in the course of one or more days, as is needed by the patient. In instances where human dosages for compounds have been established for at least some conditions, those same dosages, or dosages that are about 0.1% to about 500%, more preferably about 25% to about 250% of the established human dosage may be used. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician will know how and when to terminate, interrupt, or adjust administration due to toxicity or organ dysfunctions. Conversely, the attending physician will also know to adjust treatment to higher levels if the clinical response is not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of about 0.1 mg to 2000 mg of the active ingredient, preferably about 1 mg to about 500 mg, e.g. 5 to 200 mg. In other embodiments, an intravenous, subcutaneous, or intramuscular dose of the active ingredient of about 0.01 mg to about 100 mg, preferably about 0.1 mg to about 60 mg, e.g. about 1 to about 40 mg is used. In cases of administration of a pharmaceutically acceptable salt, dosages may be calculated as the free acid. In some embodiments, the composition is administered 1 to 4 times per day. Alternatively the compositions may be administered by continuous intravenous infusion, preferably at a dose of up to about 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the antibiotic effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. For instance, compositions can be administered using a regimen which maintains plasma levels above the MEC for 10-90% of the time, preferably between 30-90% and most preferably between 50-90%.

Compositions disclosed herein can be evaluated for efficacy and toxicity using known methods. For example, the toxicology of the compound may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

Another aspect of the present disclosure provides a method of inhibiting the proliferation of bacteria in a medium. The proliferation may involve the futalosine pathway. The method includes contacting the medium with a composition containing an effective amount of a compound or a suitable salt thereof described herein.

In some embodiments, the method targets the futalosine pathway to inhibit the production of AF. In some embodiments, the production of the aminofutalosine is catalyzed by radical SAM enzyme. In some embodiments, the radical SAM enzyme is MqnE.

The composition can be in the form of a solution, a suspension, a solid, a gel, a foam or any other form suitable for the purpose of storing and dispensing the compound or its salt and mixing it with the medium. Besides a compound of Formula I or its salt, the composition can contain one or more additional agents including for example an antibacterial agent and a proton pump inhibitor to assist with the inhibition or elimination of the target bacteria.

The medium refers to an environment, a surrounding, a substrate, or a carrier that contains the target bacteria to be controlled or eliminated. In some embodiments, the medium is a tissue, a body fluid, a culture, or a biological sample. In some embodiments, the medium is a surface or an interior of a solid, a liquid or a limited air space. In some embodiments, the medium is a food, a drink, or anything that can be consumed by a human or an animal.

The composition can be in any form for inhibiting bacterial proliferation. For example, a cleaning composition can be a solution or a gel depending on the specific use of the composition. In exemplary embodiments, the composition is a dental rinse or a hard surface cleaning solution.

The composition can also be incorporated into a kit or a device. For instance, a bandage or medical device may be impregnated with a safe and effective amount of a compound of Formula I or a salt thereof.

The amount of the compound or its salt in the composition depends on the medium and the concentration of the bacteria to be eliminated, and can be determined by one of ordinary skill in the art without undue experimentation. The composition can also contain one or more additional natural or synthetic antibiotic agents.

In another embodiment, the present disclosure proves the use of a compound as disclosed herein or a pharmaceutically acceptable salt thereof for the treatment of a bacterial infection.

The compounds disclosed herein can be prepared via various chemical procedures known to one of ordinary skill in the art. Besides the synthetic routes illustrated in the examples, other approaches can be applied in view of common chemistry knowledge and generally available references such as Advanced Practical Organic Chemistry, Routledge; 3 edition (Jan. 8, 2013) and Practical Synthetic Organic Chemistry: Reactions, Principles, and Techniques, Wiley; 2 edition (Feb. 5, 2020), the entire disclosure of these references are hereby incorporated by reference.

The following non-limiting examples serve to further illustrate the present disclosure.

EXAMPLES

Example 1

Synthesis of F-DHC compounds. DHC analogues were prepared by the methods of Hekking and Rutjes et al. as outlined in Scheme S1.

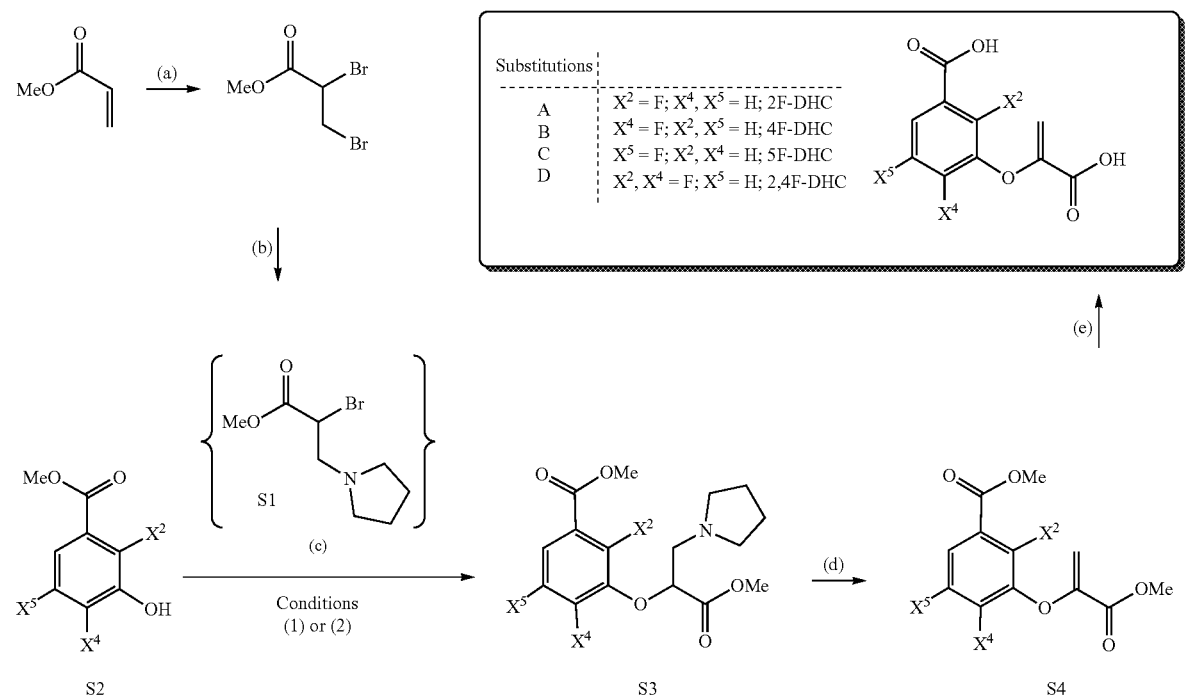

Scheme S1. General Synthetic Route to F-DHC analogues. Conditions (a) Br2, CH2Cl2, 0° C. (b) PhMe, pyrrolidine, 0° C. (c) (1) NaH, DMF, 0° C., 1 h, then crude methyl 2-bromo-3-(pyrrolidin-1-yl)propanoate in PhMe; or (2) DMF, KOtBu (1 M in THF), 0° C., 1 h then methyl 2-bromo-3-(pyrrolidin-1-yl)propanoate-1-13C in Et2O/PhMe, 0.5 h (for 13C-labelled material) (d) MeI, MeOH, Na2CO3 (or K2CO3), 60° C., 16 h (e) NaOH (aq.), Dioxane (r.t., 16 h) or MeOH (reflux, 4 h).

II. Studies of Antibacterial Activities: MqnE is Inhibited by Fluorinated Analogues of DHC The mqnE gene from *Pedobacter heparinus* (PhMqnE) was coexpressed together with the pPH151 plasmid, which contains the suf operon from *E. coli* under the control of a T7 promoter, to promote proper FeS cluster assembly in PhMqnE. Under these conditions, PhMqnE was produced in yields>50 mg/L of culture using His-trap affinity chromatography. The purified protein has $K_m$ values for SAM and DHC of 21 µM and 72 µM, respectively using the low-potential reductant dithionite (DT) as the electron source. These values are in agreement with those reported in literature for MqnE from *Thermus thermophilus*. It was surmised that positioning fluorine atoms around the aromatic ring of DHC would stabilize the captodative radical intermediate 1 by preventing it from converting to intermediate 2 in FIG. 1(a), thereby acting as a mechanism-based inhibitor and trapping the enzyme in an intermediate state. DHC analogues were synthesized with fluorine at the 2, 4, 5, and 2,4 positions of DHC (FIG. 1 (b)). In a competition assays where DHC and the fluorinated analogues were simultaneously added to the reaction at 2 mM each, all of the fluoro analogues were capable of slowing the formation of AF (FIG. 2a), ranging from ~2-fold decreases for 4F-DHC, 5F-DHC and 2,4F-DHC to ~18 fold for 2F-DHC (i.e., 3.5 $min^{-1}$ without fluoro-DHC analogs vs. 0.2 $min^{-1}$, in the presence of 2F-DHC). In these competition assays, 2F-DHC was the only inhibitor that also acted as a substrate, being converted to 2F-AF concomitant with formation of AF. In an assay with 2 mM SAM and 2 mM 2F-DHC, PhMqnE produced 2F-AF about—10 fold slower than when using DHC as a substrate (FIG. 2(b); 0.41 $min^{-1}$). In addition, assays performed with MqnE and 2 mM SAM, and 2 mM 4F-DHC or 5F-DHC could also be converted to their corresponding fluorinated AF products with rates of 1.63 and 0.38 $min^{-1}$, respectively (FIG. 2(b)). Reactions between 2,4F-DHC and SAM on the time scale of the reaction were not detected. However, the fact that 2F-DHC can effectively compete with DHC to make product while the remaining F-DHC analogues cannot, could be interpreted to mean that either 1) MqnE has a comparable or higher affinity for 2F-DHC than DHC or 2) 2F-DHC binds and reacts to initiate chemistry faster than DHC (lower commitment to catalysis), while the other F-analogues bind competitively but react slowly. To this point, when the MqnE reaction with 0.5 µM PhMqnE, 1 mM SAM and 1 mM DHC is performed in the presence of increasing concentrations of 2F-DHC the production of AF is almost completely inhibited by 250 µM 2F-DHC (FIG. 2(c)). When these data are fit to a non-linear competitive inhibition equation, a $K_i$ of ~2 µM is obtained. These data are consistent with the need for the benzoic acid moiety of DHC to be deprotonated upon binding to the enzyme because fluorination at the 2-position of benzoic acid is known to depress the pKa by ~1 unit, whereas fluorine at the 4 and 5 positions suppresses it by less than 0.2. Of note, reaction mixtures containing 2F-DHC (but not 4F- or 5F-DHC) show two additional peaks appearing during the reaction in the acid-quenched samples, which both have a positive mass-to-charge-ratio (m/z) of 478.1. The m/z of this species is consistent with a fluorinated intermediate 1 from FIG. 1(a). These two peaks form with an approximately 1:1 ratio, which likely arises from the non-stereospecific reduction and protonation of a fluorinated intermediate 1 by the reaction buffer outside of the enzyme catalytic site (i.e., DTT and solvent protons). These results indicate that inhibitors mimicking intermediate 1 may be effective against MqnE catalysis. However, when compound X was synthesized in both the R and S configuration and added them at 500 µM to an assay containing MqnE, 1 mM SAM and 1 mM DHC, no inhibition was observed (FIG. 2a). This behavior likely stems from the fact that intermediate 1 contains a radical on a tertiary carbon atom, which adopts an $sp^2$ configuration rather than $sp^3$ found in the R and S stereoisomers of compound X.

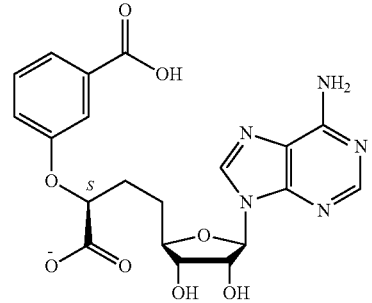

Compound X, S

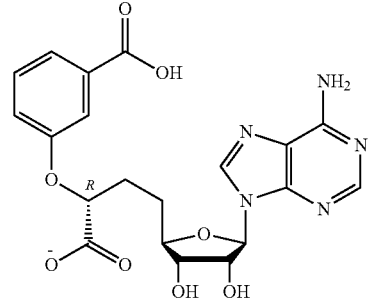

Compound X, R

F-DHC Traps an Intermediate Radical

Because acid-quenched samples of reactions containing 2F-DHC and MqnE generate a racemic mixture of fluorinated compound X, it was hypothesized that the reaction might be trapped in an intermediate state that may partially explain the inhibition seen with 2F-DHC. Therefore, a sample containing 1 mM PhMqnE, 1 mM SAM and 2 mM 2F-DHC was generated, and incubated for 5 min at room temperature (22° C.) before DT was added to initiate the reaction. The reaction was quickly loaded into an X-band EPR tube and frozen in liquid isopentane (~140° C.) in ~15 s. Analysis of the sample (denoted $^1H$ sample) by continuous-wave X-band EPR at 70 K revealed a spectrum characteristic of a carbon-based radical strongly coupled to two protons, indicated by the roughly a 1:2:1 intensity ratio of the three isolated lines. Simulation of the spectrum indicated highly isotropic $^1H$ hyperfine coupling (HF) tensors for its three principal components of both protons ($^1H1$, $^1H2$), indicating that the protons are adjacent to the radical center (Table 1).

TABLE 1

Experimental and Calculated hyperfine coupling constants (in MHz) for Intermediate 1.

| | Experiment | | | | DFT | | | |
|---|---|---|---|---|---|---|---|---|
| Nuc. | $A_1$ | $A_2$ | $A_3$ | $A_{iso}$* | $A_1$ | $A_2$ | $A_3$ | $A_{iso}$* |
| $^1H_1$ (C9) | 36.8 | 27.0 | 39.0 | 34.3 | 22.1 | 22.5 | 34.5 | 26.4 |
| $^1H_2$ (C9) | 18.8 | 24.9 | 32.6 | 25.4 | 18.4 | 18.8 | 31.5 | 22.9 |
| $^1H_3$ (C5') | -8.5 | 8.5 | 8.5 | 2.8 | -7.4 | -4.7 | 3.5 | -2.9 |
| $^1H_4$ (C5') | 1.0 | 1.0 | 7.0 | 3.0 | 4.5 | 5.8 | 12.0 | 7.5 |

TABLE 1-continued

Experimental and Calculated hyperfine coupling constants (in MHz) for Intermediate 1.

| Nuc. | Experiment | | | | DFT | | | |
|---|---|---|---|---|---|---|---|---|
| | $A_1$ | $A_2$ | $A_3$ | $A_{iso}$* | $A_1$ | $A_2$ | $A_3$ | $A_{iso}$* |
| $^{19}F_1$ (C2) | −1.0 | −1.0 | 9.0 | 2.3 | −1.2 | −0.3 | 9.4 | 2.6 |
| $^{13}C_1$ (C5') | 56.6 | 71.0 | 56.6 | 61.4 | 56.1 | 56.4 | 69.4 | 60.8 |
| $^{13}C_2$ (C4') | 2.0 | 2.0 | 3.0 | 2.3 | −2.3 | −2.1 | −0.7 | −1.7 |
| $^{13}C_3$ (C3') | 0.5 | 0.5 | 2.0 | 1.0 | 0.9 | 1.0 | 1.6 | 1.2 |
| $^{14}N$ (?)** | 1.5 | 1.2 | 0.7 | 1.1 | n.a. | n.a. | n.a | n.a. |

*$A_{iso}$ is a mean value of $A_1$, $A_2$ and $A_3$.
**Quadrupole coupling constants associated with this nucleus are K = 0.34 MHz and η = 0.73.

Figure 1A:
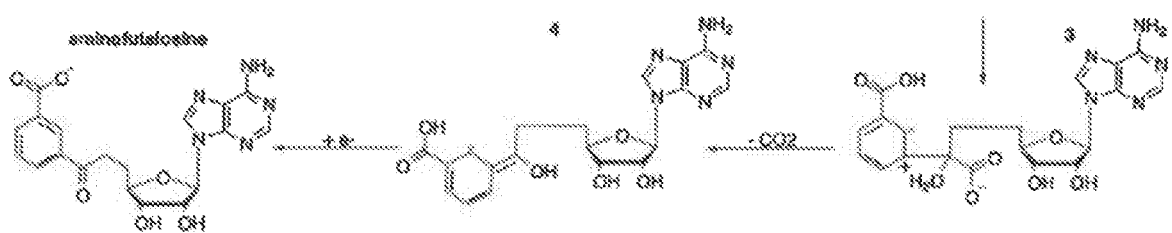
Figure 1B:
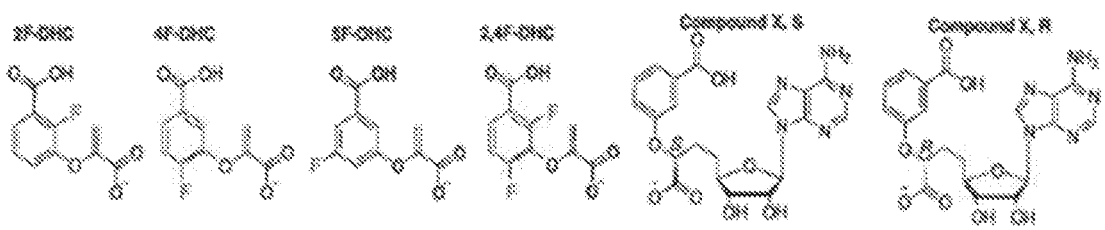
Figure 2A:
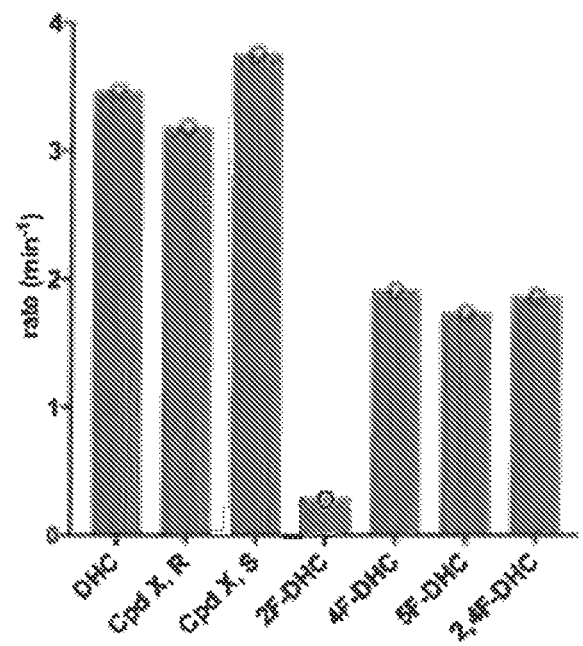
FIGS. 2(a), 2(b) and 2(c) illustrate inhibition studies of MqnE.
Figure 2B:
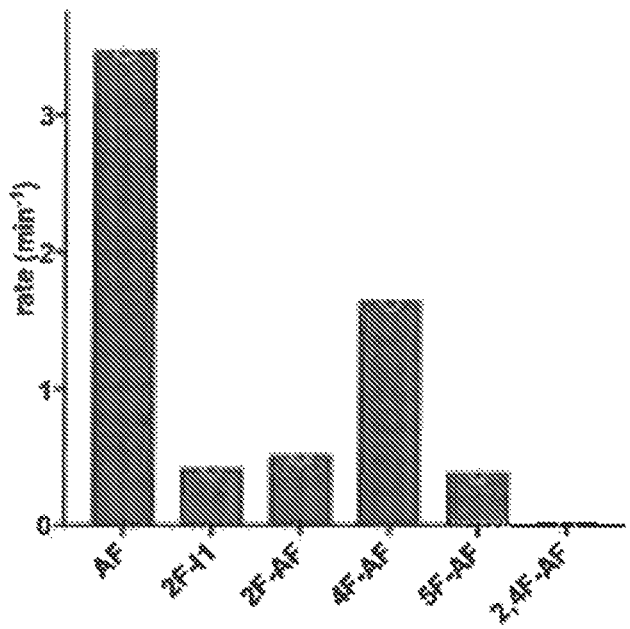
Figure 2C:
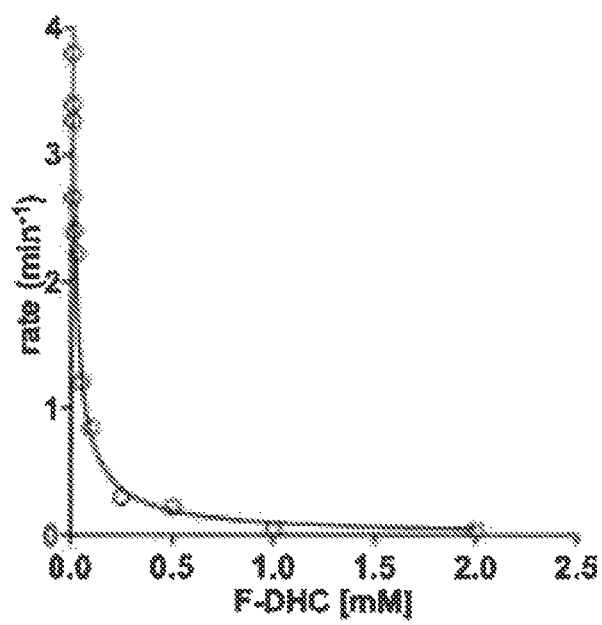
Figure 4A:
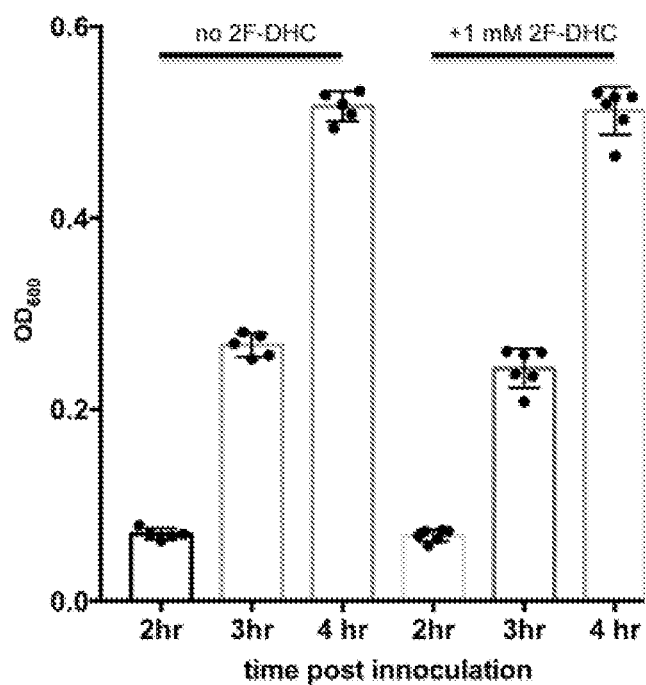
FIGS. 4(a) and 4(b) illustrate *E. coli* and HEK293T cell growth in the presence of 2F-DHC.
Figure 4B:
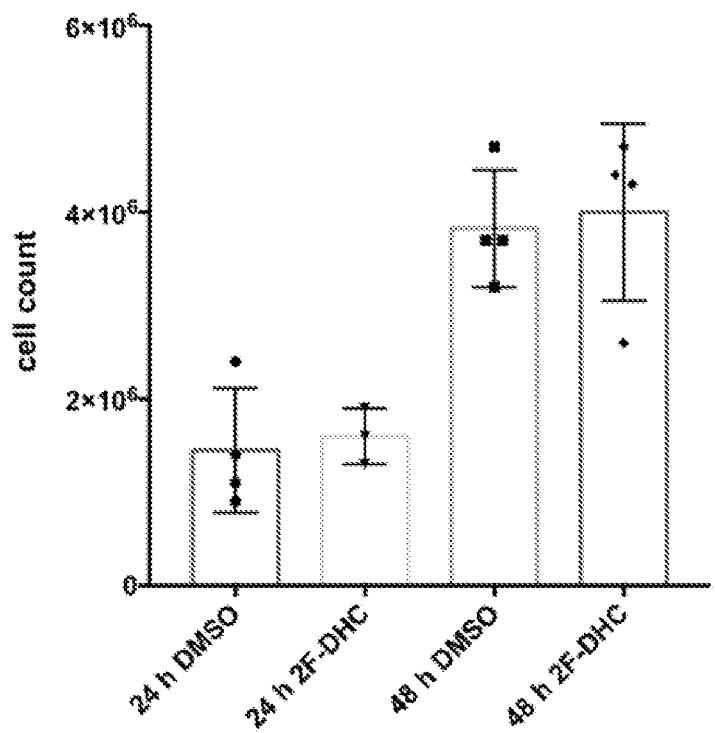

The intermediate species was assigned as 2F-intermediate 1—containing a fluorine atom at position 2 of the DHC ring—in FIG. 1(a). To provide further evidence for this assignment, SAM containing $^{13}C$ in all carbon positions in the adenosine moiety was used to generate a sample (denoted $^1$1-1-$^{13}C$ sample) as above. The EPR spectra could not be fully simulated with the above parameters that also include only one strongly coupled $^{13}C$ center. Initially, it was considered that two $^{13}C$ carbon centers were strongly interacting with the radical in this intermediate based on best-fit simulations. However, this interpretation contradicts the expected electronic structure that implies the presence of only a single strongly coupled $^{13}C$ nucleus (C5'). Moreover, Q-band ENDOR measurements reveal a $^{13}C$ hyperfine coupling interaction of a magnitude that is also incompatible with this interpretation. Another possibility was that the $^{13}C$ sample was contaminated with $^{12}C$-SAM that originated from the purified PhMqnE. Indeed, when a reaction was run with 100 pM PhMqnE in the presence of DT, 1 mM DHC and no SAM, ~30 μM of AF was generated. If a ~30% contribution from $^{12}C$-SAM was subtracted from the spectra, the spectra with only one strongly coupled $^{13}C$ carbon with an hyperfine coupling constant was simulated, consistent with the one obtained from the $^{13}C$ ENDOR measurements. To fully characterize the electronic structure of 2F-intermediate 1, additional HYSCORE experiments were performed on both the $^1H$ and $^1H$-$^{13}C$ samples from above. The signals for the two strongly coupled protons, $^1$ft and $^1H2$, are present. The spectrum also clearly shows two weakly coupled proton signals (see $^1H3$ and $^1H4$ in Table 1). When the $^1H$-$^{13}C$ sample was analyzed, peaks for two additional, weakly coupled $^{13}C$ centers were observed (see $^{13}C_2$, $^{13}C_3$ in Table 1). The $^{13}C_1$ hyperfine coupling interaction is too strong to be effectively observed in HYSCORE experiments, which favor relatively weak, predominantly anisotropic hyperfine coupling interactions. To obtain a more precise depiction of the electronic structure of 2F-intermediate 1 and to assign the observed hyperfine interactions, density functional theory (DFT) calculations were performed. Table 1 includes comparisons of the calculated hyperfine coupling constants with those derived experimentally. The agreement between the experimental and theoretical values is high, confirming the localization of spin density in 2F-intermediate 1. In addition, the structure of the calculated 2F-intermediate 1 confirms that the stereochemistry of the radical located on carbon 8 atom (numbering from Figure TA) is sp$^2$, agreeing with the lack of inhibition that was observed when using compound X in inhibition assays. The HYSCORE spectra in FIGS. 4(a)-(c) show a relatively strong $^{14}N$ hyperfine coupling interaction. This signal was tentatively assigned as arising from a nitrogen residing in the protein scaffold that is in sufficiently close proximity to interact with the radical center. In addition, at lower temperatures around 10K, a second, fast relaxing EPR species was identified with substantially different relaxation properties than that of intermediate 1. The most likely explanation for these differences in the McinE active site is the proximity of the radical species to the RS [4Fe-4S] cluster. Using these differences in power saturation properties, the spectra of the species X was extracted from both the $^1H$ and $^1H$-$^{13}C$ samples. The spectra from the two samples are very similar—the $^{13}C$ contribution from SAM in this intermediate is not evident. The spectra could be interpreted using three roughly isotropic $^1H$ hyperfine coupling constants with $A_{iso}$ of 29 MHz, 29 MHz and 32 MHz (see supporting information for details). Because this species is not coupled with neither $^{13}C$ centers nor the $^{19}F$ center found in the 2F-DHC, this species could not be attributed to any intermediate on the pathway. It was believed this species could be an abortive side reaction, where the radical "hops" to the protein skeleton, effectively ending the catalytic cycle. However, this remains to be evaluated.

Example 3

F-DHC Selectively Inhibits Hp Growth

Figure 3A:
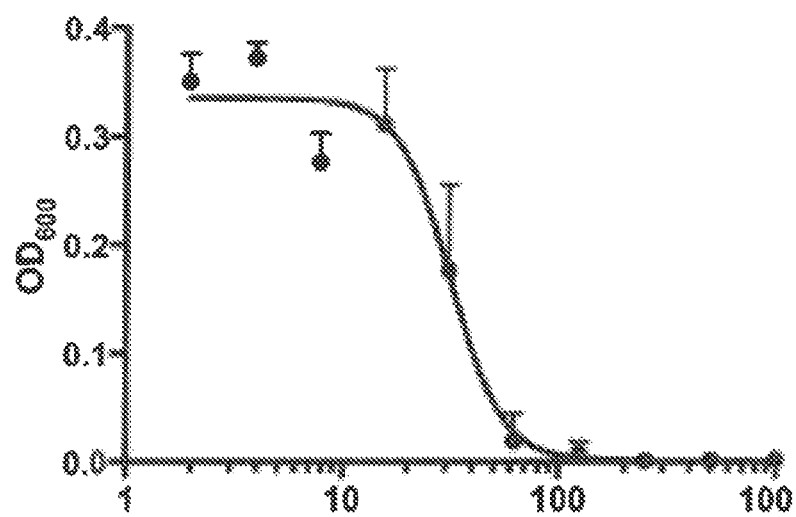
FIGS. 3(a) and 3(b) illustrate inhibition of *H. pylori* growth in vivo by 2F-DHC is specific to the futalosine pathway.
Figure 3B:
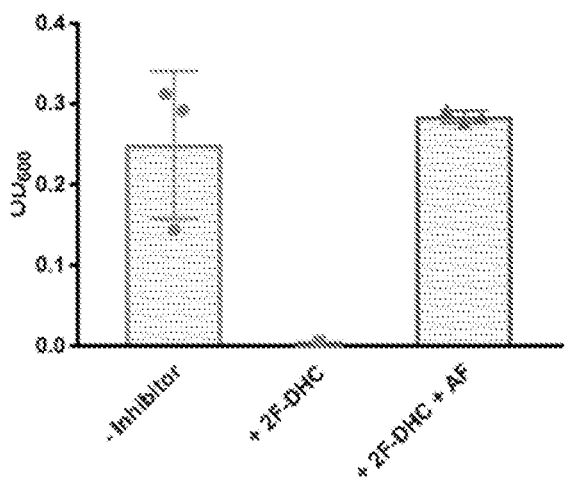

Hp grows under microaerobic conditions in the human gut, where over population can lead to ulcers and cancer. Based on the K results described above, the effects of 2F-DHC were examined on the growth of Hp in BHI medium supplemented with 10% fetal bovine serum and Hp selective supplement (DENT supplement) in 96-well plate format. Growth of Hp was detected by measuring the optical density of the media at 600 nm after 72 hr of growth at 37° C. (FIG. 3(a)). At a concentration of ~30 μM (6 pg/mL), 2F-DHC inhibits the growth of Hp by about 50% (1050=31.8±2.5), whereas at a concentration of 100 μM (23 pg/mL) the growth is completely inhibited. The minimal inhibitory concentration that restricts >90% of the growth (IC90) for 2-FDHC is <23 μg/mL, which is comparable to the vinyl sulfonamide inhibitors (~6 μM) that target MenE or the allylaminomethanone-A and phenethylaminomethanone-A inhibitors (1.5 and 12.5 pg/mL, respectively) that target MenA in the canonical MK pathway. As a control, the effects of 2F-DHC on the growth of *Escherichia coli* in minimal media were examined, and as expected there was no effect. To determine if 2F-DHC inhibits Hp growth by specifically blocking the action of MqnE in the futalosine pathway, it was tested whether the product of MqnE, AF, could rescue Hp growth in the presence of 2F-DHC. When Hp is grown as above, the culture reaches and $OD_{600}$ of—0.24 after 48 hr (FIG. 3b, −inhibitor), whereas the addition of 1 mM 2F-DHC completely inhibits growth of Hp (FIG. 3b, 2F-DHC). However, when the media was supplemented with 1 mM AF, the growth of Hp was fully restored and the cultures again reached an $OD_{600}$ of ~0.28 after 48 hr. These results are consistent with a mechanism of action in which 2F-DHC inhibits the growth of Hp by directly targeting MqnE.

This evidence indicates that a 2F-DHC-substrate analogue is capable of inhibiting MqnE catalysis. Complementary CW and HYSCORE EPR data support an intermediate that accumulates during the reaction between MqnE and 2F-DHC is consistent with intermediate 1 from FIG. 1(a). These data show that the inhibition associated with 2F-DHC is due to the reduced rate of decay of an intermediate generated during catalysis and provide the first strong evidence for an intermediate in the reaction. In addition, it is shown that 2F-DHC is capable of inhibiting the growth of Hp in a species-selective fashion by directly and specifically targeting MqnE of the futalosine pathway for MK biosynthesis.

FIGS. 4(a) and 4(b) further demonstrate that 2F-DHC is specific for Hp inhibition and does not inhibit human cells or E. coli cells, which do not have the MqnE pathway. As shown in FIG. 4(a), an overnight culture of E. coli was diluted 1:25 into 100 μL of minimal media with either 1 μL of DMSO (no DHC control) or 1 μL of 100 mM 2F-DHC in DMSO in a 96-well plate. The plate was shaken at 37° C. and monitored for at 2, 3, and 4 hr post inoculation by measuring the $OD_{600}$. No difference in growth is observed. FIG. 4(b) shows a 24 and 48 hr culture of HEK293T cells grown in FreeStyle Expression Medium containing either 1% DMSO (no DHC control) or 1 mM 2F-DHC in DMSO in a 24-well plate. Cell growth and viability were measured with an automated cell counter after staining with tryptan blue (Countess, Life Technologies). No difference in growth is observed.

It will be appreciated by persons skilled in the art that invention described herein are not limited to what has been particularly shown and described. Rather, the scope of the invention is defined by the claims which follow. It should further be understood that the above description is only representative of illustrative examples of embodiments. The description has not attempted to exhaustively enumerate all possible variations. The alternate embodiments may not have been presented for a specific substituent of the compound or composition, or a step of the method, and may result from a different combination of described substituent or agent, or that other undescribed alternate embodiments may be available for a compound or composition or method, is not to be considered a disclaimer of those alternate embodiments. It will be appreciated that many of those undescribed embodiments are within the literal scope of the following claims, and others are equivalent.

All references cited herein are incorporated herein in their entireties.

The invention claimed is:

1. A compound or a pharmaceutically acceptable salt thereof, wherein the compound is represented by Formula I,

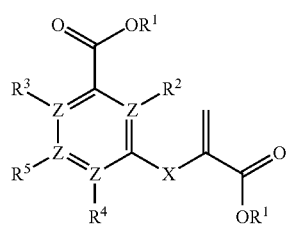

Formula I wherein:

$R^1$ in each instance independently is hydrogen or $C_{1-10}$alkyl, wherein the $C_{1-10}$alkyl is optionally substituted with one or more selected from the group consisting of a halogen, oxo (=O), OH, $OC_{1-4}$alkyl, $SC_{1-4}$alkyl, and aryl$C_{1-6}$alkyl;

$R^2$, $R^3$, $R^4$, and $R^5$ are each independently selected from the group consisting of hydrogen, fluorine, chlorine, bromine, $C_{1-4}$alkyl, CN, $C_{1-6}$alkylCONH, $C_{1-6}$alkylNHCO, $C_{1-6}$alkylSO$_2$NH, $C_{1-6}$alkylNHSO$_2$, and $C_{1-6}$alkylSO$_2$;

X is O, S, NH or CH$_2$;

and

Z in each instance independently is C or N, provided that:
when a Z is N, the substituent $R^2$, $R^3$, $R^4$, or $R^5$ attached thereto is void; and
when each Z is C, at least one of $R^2$, $R^3$, $R^4$, and $R^5$ is chlorine or fluorine.

2. The compound or the pharmaceutically acceptable salt thereof of claim 1, wherein the compound is represented by Formula I-c,

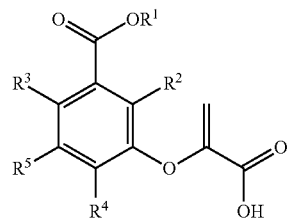

wherein
$R^1$ is hydrogen or $C_{1-6}$alkyl;
$R^2$, $R^3$, $R^4$, and $R^5$ are each independently selected from the group consisting of hydrogen, fluorine, chlorine, and $C_{1-6}$alkyl.

3. The compound or the pharmaceutically acceptable salt thereof of claim 1, wherein $R^1$ is hydrogen.

4. The compound or the pharmaceutically acceptable salt thereof of claim 1, wherein at least one of $R^2$, $R^3$, $R^4$, and $R^5$ is fluorine.

5. The compound or the pharmaceutically acceptable salt thereof of claim 1, wherein $R^2$, $R^3$, $R^4$, and $R^5$ are each independently hydrogen or fluorine.

6. The compound or the pharmaceutically acceptable salt thereof of claim 1, wherein the compound is selected from the group consisting of

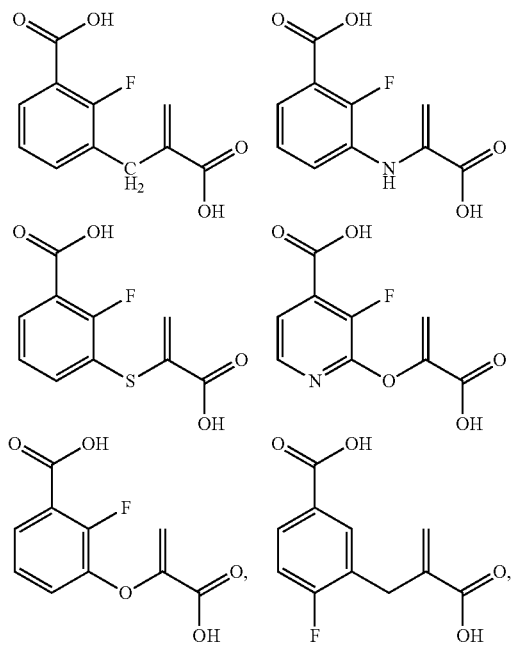

-continued

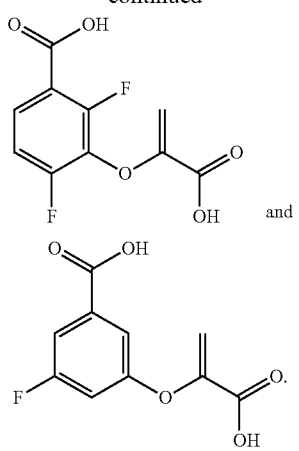
and

7. A pharmaceutical composition comprising the compound or the pharmaceutically acceptable salt thereof of claim 1.

8. The pharmaceutical composition of claim 7, wherein the compound is selected from the group consisting of

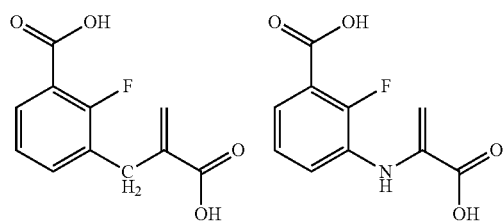

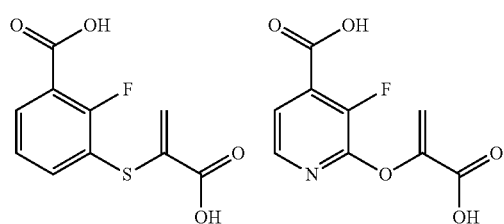

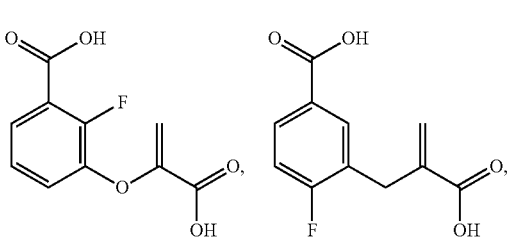

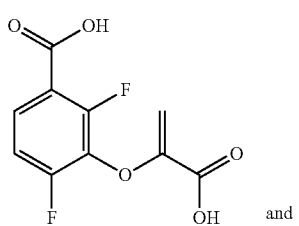
and

-continued

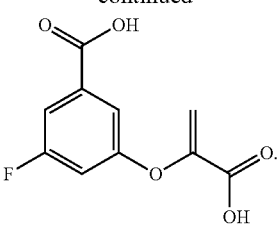

9. A method of treating a bacterial infection or inhibiting the proliferation of bacteria in a subject in need thereof, which comprises administering to the subject a therapeutically effective amount of the compound or the pharmaceutically acceptable salt thereof of claim 1.

10. The method of claim 9, wherein the compound or the pharmaceutically acceptable salt thereof is selective for the bacteria over *Clostridium difficile, Escherichia coli* or any other species that lacks the futalosine pathway.

11. The method of claim 9, wherein the bacteria belongs to a genus selected from the group consisting of *Helicobacter, Campylobacter, Streptococcus, Clostridium, Mycoplasma, Lactobacillus, Staphylococcus, Bifidobacterium, Rickettsia*, and *Brucella*.

12. The method of claim 9, wherein the bacteria belongs to *Helicobacter* genus.

13. The method of claim 9, wherein the bacteria is *Helicobacter pylori*.

14. The method of claim 9, wherein the subject is a human.

15. The method of claim 9, wherein the compound is selected from the group consisting of

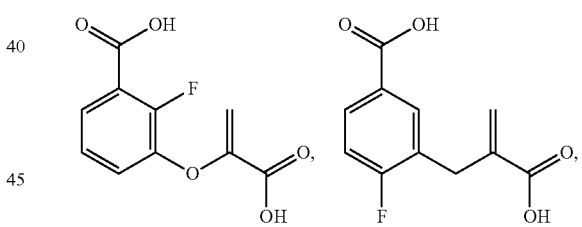

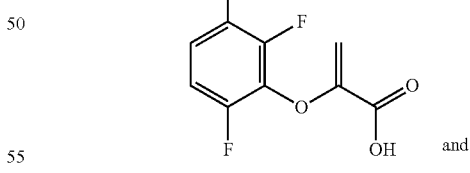

16. The method of claim 9 wherein the bacteria is *Helicobacter pylori* and the compound is

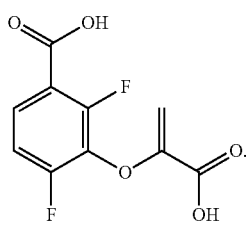 [SMILES: C=C(Oc1c(F)ccc(C(=O)O)c1F)C(=O)O]

17. A method of inhibiting MqnE in a bacterial cell, comprising contacting the cell with an effective amount of the compound or the pharmaceutically acceptable salt thereof of claim 1.

18. The method of claim 17, wherein the bacterial cell belongs to a genus selected from the group consisting of Helicobacter, Campylobacter, Streptococcus, Clostridium, Mycoplasma, Lactobacillus, Staphylococcus, Bifidobacterium, Rickettsia, and Brucella.

19. The method of claim 17, wherein the bacterial cell is Helicobacter pylori.

20. The compound or a pharmaceutically acceptable salt thereof of claim 1, wherein the compound is

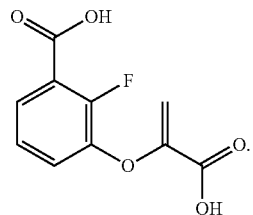 [SMILES: C=C(Oc1cccc(C(=O)O)c1F)C(=O)O]

* * * * *